Figure 1:
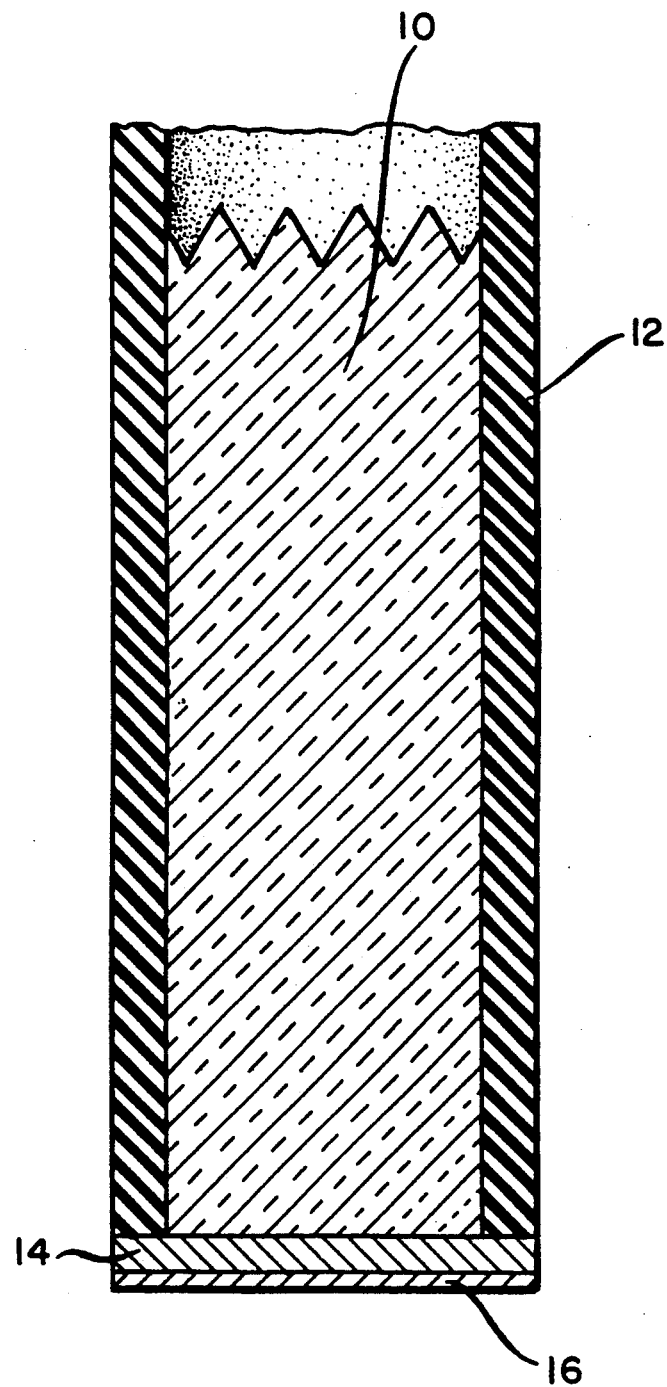

United States Patent [19]

Walker, Jr.

[11] Patent Number: 4,988,588

[45] Date of Patent: Jan. 29, 1991

[54] MINIATURE POROUS ELECTRODE AND METHOD OF MAKING

[75] Inventor: Charles W. Walker, Jr., Neptune, N.J.

[73] Assignee: The United States of America as represented by the Secretary of the Army, Washington, D.C.

[21] Appl. No.: 527,964

[22] Filed: May 24, 1990

[51] Int. Cl.$^5$ .............................................. H01M 4/02
[52] U.S. Cl. ...................................................... 429/209
[58] Field of Search .................... 429/209, 8; 204/435, 204/290 R, 291, 279, 280

[56] References Cited

U.S. PATENT DOCUMENTS

| 2,968,688 | 1/1961 | Skinner | 429/8 |
| 3,000,804 | 9/1961 | Cahoon et al. | 204/435 X |
| 3,810,828 | 5/1974 | Lindholm | 429/209 X |

Primary Examiner—Anthony Skapars
Attorney, Agent, or Firm—Michael Zelenka; Roy E. Gordon

[57] ABSTRACT

A miniature electrochemically active porous material cathode for electrochemical studies is made from a conductive rod that is sheathed in electrical insulation except for the cross sectional area at one end of the rod by coating said cross sectional area with a thin layer of conductive epoxy and, prior to curing, pressing the conductive epoxy in contact with electrochemically active porous cathode material.

4 Claims, 3 Drawing Sheets

MINIATURE POROUS ELECTRODE AND METHOD OF MAKING

The invention described herein may be manufactured, used, and licensed by or for the Government for governmental purposes without the payment to me of any royalty thereon.

This invention relates to a miniature porous electrode for electrochemical studies and to its method of making.

BACKGROUND OF THE INVENTION

Electrochemical studies with solid, stationary electrodes have usually employed noble metals (e.g. platinum, gold) and carbon. Advantages offered by these materials include easy fabrication into an electrode, large useful potential range, and good electrical conductivity and reproducibility.

Very often, mechanistic, kinetic and diagnostic studies are performed with small electrodes fashioned into rods which are insulated except for the cross-sectional area at one end of the rod (typical diameter of 3 mm). To increase reproducibility, the electrode is high polished to ensure a like surface from experiment to experiment.

Many battery systems employ carbons with surface areas of 60-1500m$^2$/gram to construct porous cathodes. Binders (e.g. teflon or other polymers) are used to hold the carbon particles together. Direct comparison of porous carbon electrodes with glassy carbon or metal rod electrodes is difficult since porous carbon cathodes are necessarily large and thick (by comparison) in order to maintain mechanical integrity during and after fabrication. Rods of metal or glassy carbon as described above have surface areas nearly equal to the 2-dimensional geometric area one measures. Multiplying the area of glassy carbon to "scale up" surfaces to reflect that of various 3-dimensional porous carbons is not valid, especially since structures, end groups and properties vary between each manufacturer of carbon. A method of preparing a very thin, miniature porous carbon cathode on scale with glassy carbon rod electrodes would be desired so that carbons could be easily and rapidly ranked for electrochemical characteristics in small laboratory test cells rather than the present practice of preparing large glass laboratory cells or hermetically sealed cells. Further, elimination of binder materials would provide one less variable to be considered for comparison studies.

The study of electrochemically formed conducting polymers and their use in electrochemical systems as cathode materials has recently become of interest. Films can be directly polymerized onto conductive substrates (e.g. platinum). One attribute of polymer films (in the range of 1-20 μm thick) is that the magnified surface is very rough, meaning the true surface area is several times that of the measured 2-dimensional area. Since these polymer films have porous structures it is of interest to rank/rate the performance of these films with more conventional and extensively studied porous carbon cathodes. A porous cathode of similar dimensions is required for a fair comparison.

Small carbon paste electrodes have been described that include a platinum (or other material) contact inserted into a teflon well. The well is then filled with a paste of graphite powder and mulling liquid such as mineral oil. Problems include finding a pure mulling agent which is electroinactive over the potential range of interest; completely filling the well to eliminate void; drying out; excessive pressure separating oil and carbon. Although useful in aqueous solutions, carbon paste electrodes in nonaqueous (e.g. acetonitrile, propylene carbonate) solutions tend to disintegrate. Also, they are relatively thick electrodes.

Swofford and Carman (Anal. Chem. 38, 966, 1966) reported on an electrode consisting of a carbon-epoxy resin suspension. However, the maximum amount of carbon was only 25%, and the electrode was polished to a smooth finish (low surface area). Pungor, Szepesvary and Havas (Anal. Lett. 1, 213, 1968) prepared a graphite impregnated silicone rubber electrode that was vulcanized at room temperature. The electrode was used in voltammetric analysis and the surface renewed by cutting off the end of the spent rod.

Obviously, the two previous techniques employ rigid matrices impregnated with carbon or graphite to provide electrical conductivity and an electrochemically active surface. Both methods provide a low surface area electrode and neither method enables one to observe properties of the carbon itself as a porous structure.

SUMMARY OF THE INVENTION

The general object of this invention is to provide a miniature porous electrode for electrochemical studies and a method of making such an electrode. A more particular object of the invention is to provide such a method wherein the porous material is the electroactive substance. A still further object of the invention is to provide such a method wherein the dimensions of the area comprising the active electrode are smaller than those normally required to make a mechanically sound porous electrode. Another object of the invention is to provide such an electrode and method of making wherein the porous material is fashioned into a very thin layer upon a suitable substrate. Another object of the invention is to provide such an electrode and method of making that is amenable for electrode construction using any number of porous materials. A still further object of the invention is to provide such a method that avoids the incorporation of binders or mulling agents within the porous structure.

It has now been found that the aforementioned objects can be attained and a miniature porous electrode for electrochemical studies obtained from a conductive rod that is sheathed in electrical insulation except for the cross section area at one end of the rod by coating said cross sectioned area with a thin layer of conductive epoxy and, prior to curing, pressing the conductive epoxy into contact with the electrochemically active porous electrode material.

DESCRIPTION OF THE DRAWING AND THE PREFERRED EMBODIMENT

In the manufacture of the miniature porous electrode according to the invention, the end of a glass carbon rod or other conductive substrate is coated with a thin layer of conductive epoxy. Prior to its curing, the epoxy covered end is pressed or tamped firmly several times into a shallow dish or test tube containing the powdery material of interest. Pressure ensures good contact between the epoxy and porous material. After allowing the epoxy to dry, any excess material and/or epoxy is removed. The conductive rod or substrate is sheathed in an electrically insulating material, exposing only the end containing the electrochemically active porous material. Electrical leads may be attached to the opposite end of the rod.

FIG. 1 shows a miniature porous electrode according to the invention.

Figure 2:
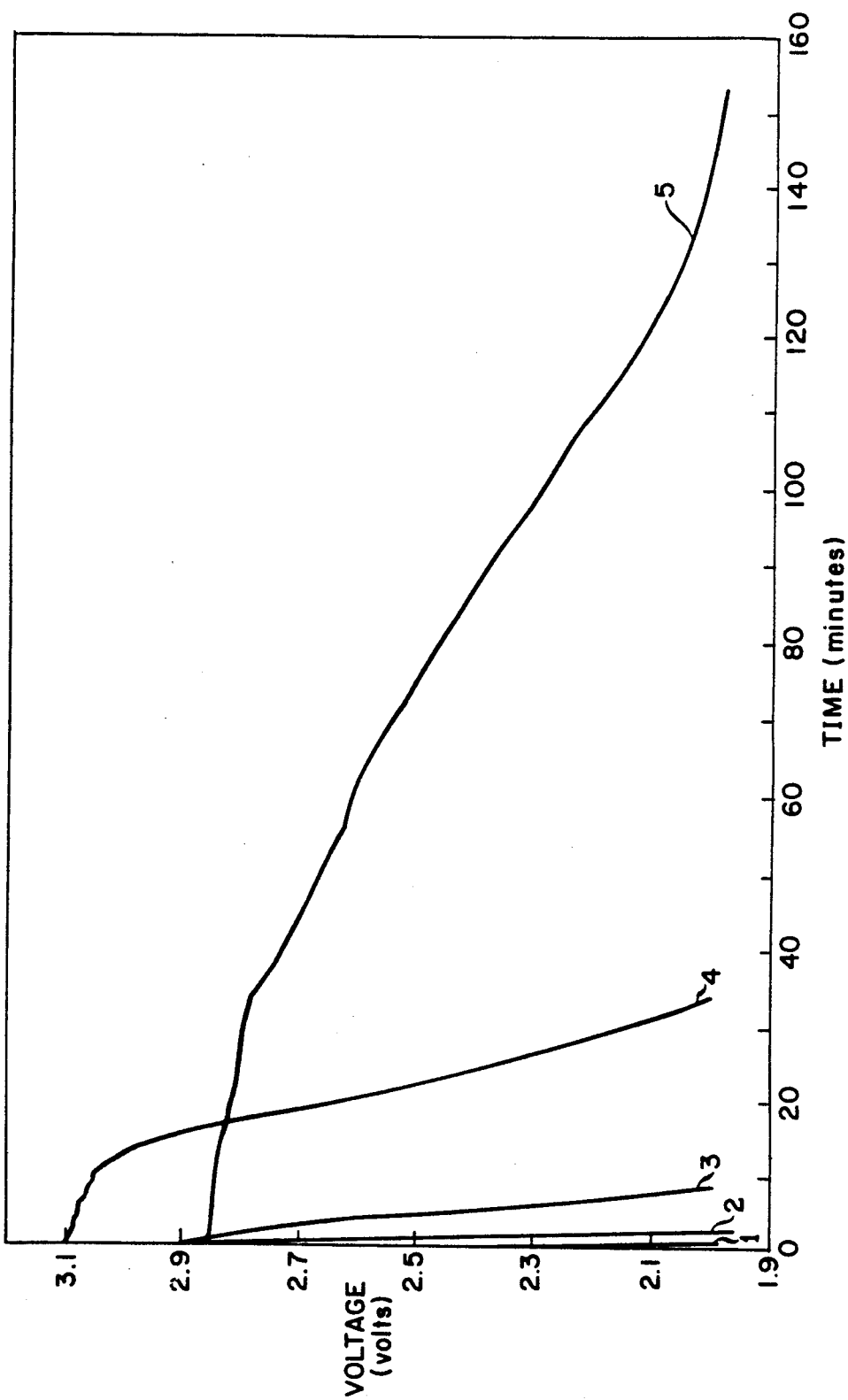

FIG. 2 is a discharge curve showing various electrodes discharged at 0.05 mA/cm$^2$ in LiAlCl$_4$-3SO$_2$ vs lithium wherein the ordinate is the voltage in volts and the abscissa is time in minutes. Discharge curve 1 is for glassy carbon coated with silver epoxy. Discharge curve 2 is for glassy carbon as received. Discharge curve 3 is for glassy carbon polished smooth. Discharge curve 4 is for platinum polished smooth. Discharge curve 5 is for porous carbon electrode of Shawinigan acetylene black on glassy carbon attached via silver epoxy.

Figure 3:
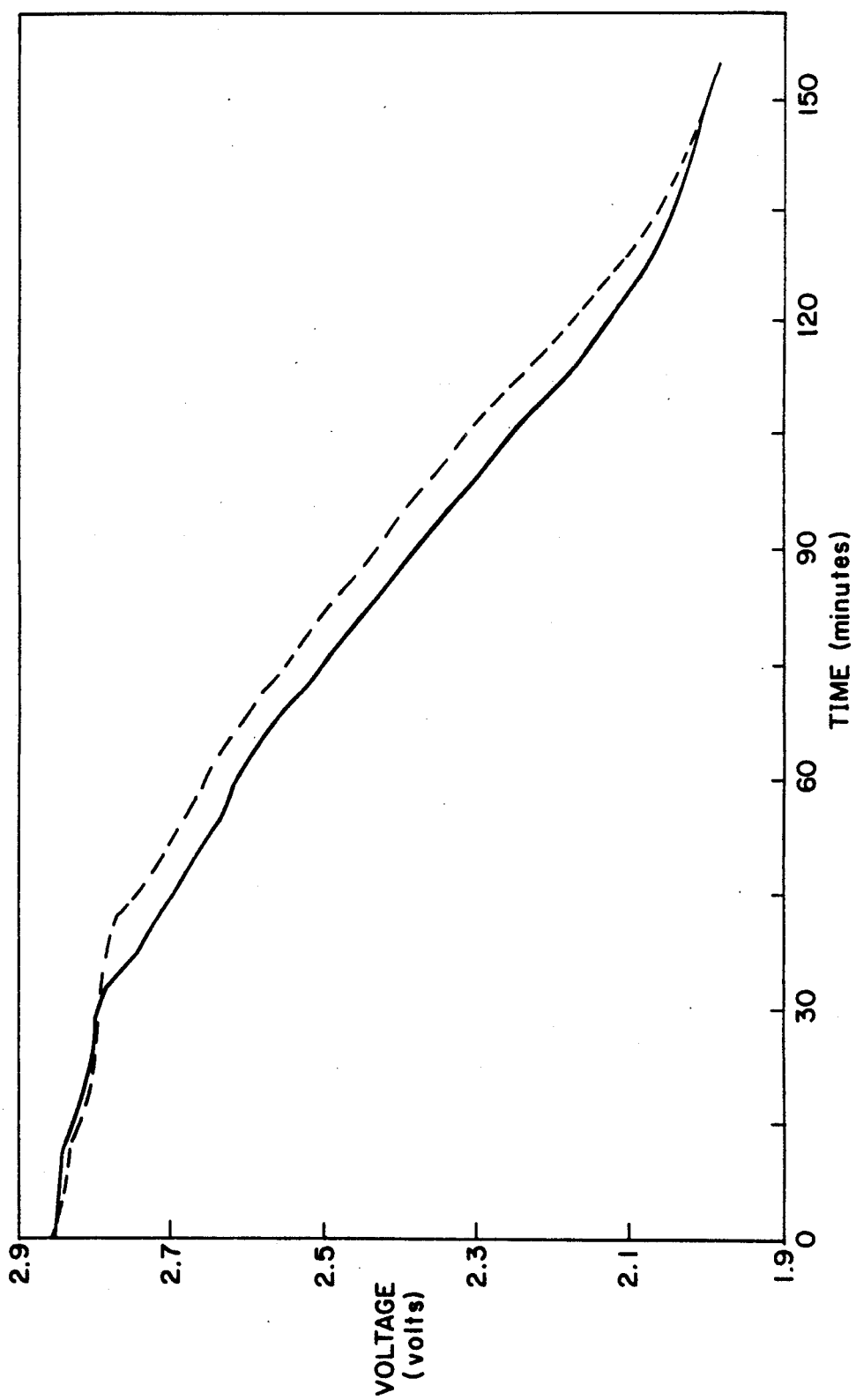

FIG. 3 is a discharge curve showing voltage versus time for the first discharge of a newly constructed electrode and the second discharge after regeneration. The solid line is first discharge and the dashed line is second discharge.

Referring to FIG. 1, a glassy carbon rod, 10, or any other conductive substrate of desired size and shape is sheathed in electrically insulating material such as heat shrink teflon 12, Kel-F, glass etc. A thin film of conductive silver epoxy, 14, is applied to the exposed end that is then brought in contact with the porous material to be studied, 16. The conductive epoxy can be any conductive epoxy, including epoxy that is made conductive by incorporating the porous material of interest.

EXAMPLE 1

Two part conducting epoxy (silver-containing AESAR Mattheylec A-500) is applied to the end of glassy carbon rods (0.07 cm$^2$ cross sectional area) that are sheathed in heat shrink teflon for electrical insulation. The rods are firmly pressed repeatedly into a dish containing (powdered) Gulf AB50P acetylene black (Gulf Oil, Baytown, Tex.). Rods are then dried at 50° C. for one hour and then overnight at 50° C. under vacuum. Excess carbon and epoxy are shaved away with a scalpel blade. Carbon loading is difficult to precisely control during fabrication, so additional steps are taken to ensure equal loading of material onto the rods. Rods are dipped into a test tube containing a mixture of distilled water and acetone, then gently shaken and tapped against the walls of the tube to knock off most of the carbon except a thin layer adhering to the epoxy. Electrodes are again dried at 50° C. under vacuum.

Removal of carbon requires some skill to remove the appropriate amounts. Note that acetone is needed to assist wetting of the carbon (using water alone will not wet). Use of an ultrasonic bath can be useful but is found to remove too much carbon for this application. Under 80X magnification some irregularities resembling small "hills" are observed. Lightly rubbing the end of the rod on a piece of paper removes the excess carbon ("hills") and smooths out the surface to give an even contour.

EXAMPLE 2

Porous carbon electrodes are prepared as in Example 1. Controls are also prepared glassy carbon polished to a mirror surface, platinum polished to a mirror surface, glassy carbon as received, and glassy carbon with silver conducting epoxy on the end. All electrodes are sheathed in teflon and have measured surface areas of 0.07 cm$^2$. An inorganic electrolyte, LiAlCl$_4$-3SO$_2$ is used in a glass test cell containing a lithium metal anode and a lithium reference electrode. The 0.07 cm$^2$ rods are used as cathodes. Constant current discharges of 0.05 cm$^2$ are performed on each rod to a 2.0 volt cutoff. The discharge product of this electrolyte fouls the surface of the cathode and is responsible for cell failure as the electroactive surface becomes passivated. It is expected that the high surface area of the porous carbon electrode will remain active longer than the other materials and result in the longest discharge. FIG. 2 shows the results. As expected, low surface area glassy carbon, platinum and epoxy-coated electrodes provide very little capacity since they are quickly passivated with discharge product. The high surface area porous carbon has a very long capacity. This reflects the high area imparted to the rod.

EXAMPLE 3

Careful handling permits renewal and reuse of the electrodes. A porous carbon electrode (as in Example 1) is discharged in a cell as in Example 2. After discharge the electrode is removed from the cell and allowed to stand in warm water for five minutes. The passivating discharge product is water soluble, and is effectively removed by this "washing" procedure. The electrode is rinsed in distilled water, dried under vacuum at 50° C. and replaced in the cell. The electrode is again discharged under identical conditions and provides the same capacity that is observed during the initial discharge. This data is illustrated in FIG. 3. The successful renewal of the electrode attests to the mechanically sound nature of the electrode.

EXAMPLE 4

The epoxy covered rod has an open circuit voltage (OCV) of 2.79 V and yields insignificant capacity when discharged (FIG. 2). When used in the construction of a porous carbon electrode the epoxy influenced the open circuit potential of the system. Porous carbon should give an open circuit voltage (OCV) of 3.3 to 3.4 V, as does glassy carbon. Instead, due to the thin nature of the porous carbon film the OCV of the system consists of a mixed potential of carbon and epoxy (OCV=2.87 V). Porous electrodes containing a thicker film of porous carbon more closely reflect the OCV of the carbon Results are tabulated below:

| OCV (volts) | Electrode |
| --- | --- |
| 3.3 to 3.4 | Glassy carbon, polished |
| 2.79 | Glassy carbon coated with silver epoxy |
| 2.87 | Thin film porous carbon (with silver epoxy) |
| 3.1 | Thick film porous carbon (with silver epoxy) |

A way to avoid mixed potentials other than making thicker electrodes is to render non-conductive epoxy conductive by mixing in a sufficient amount of the porous material to be studied. In this way, the epoxy will be electrically conducting and will maintain compatible materials throughout the system. This will eliminate formation of mixed potentials. Insignificant discharge of the epoxy will occur because of its low surface area.

I wish it to be understood that I do not desire to be limited to the exact details of construction shown and described for obvious modifications will occur to a person skilled in the art.

What is claimed is:

1. A miniature porous electrode for electrochemical studies comprising a conductive rod that is sheathed in electrical insulation except for the cross sectional area at one end of the rod, a thin layer of conductive epoxy coating on said cross sectional area and a porous electrochemically active material for electrochemical study in contact with the conductive epoxy and electrical leads attached to the opposite end of the rod.

2. A miniature porous electrode according to claim 1 wherein the conductive rod is a glassy carbon rod.

3. A miniature porous electrode according to claim 1 wherein the rod is sheathed in heat shrink teflon for electrical insulation.

4. A miniature porous electrode according to claim 1 wherein the electrochemically active material of interest is acetylene black.

* * * * *